United States Patent
Steel et al.

(10) Patent No.: US 8,699,029 B2
(45) Date of Patent: Apr. 15, 2014

(54) MINIATURIZED LASER HETERODYNE RADIOMETER FOR CARBON DIOXIDE, METHANE AND CARBON MONOXIDE MEASUREMENTS IN THE ATMOSPHERIC COLUMN

(75) Inventors: Emily W. Steel, Edgewater, MD (US); Matthew L. McLinden, Greenbelt, MD (US)

(73) Assignee: The United States of America as represented by the Administrator of the National Aeronautics Space Administration, Washington, DC (US)

( * ) Notice: Subject to any disclaimer, the term of this patent is extended or adjusted under 35 U.S.C. 154(b) by 20 days.

(21) Appl. No.: 13/545,173

(22) Filed: Jul. 10, 2012

(65) Prior Publication Data
US 2014/0016134 A1    Jan. 16, 2014

(51) Int. Cl.
*G01N 21/00*    (2006.01)
(52) U.S. Cl.
USPC .......................................... 356/437; 356/440
(58) Field of Classification Search
USPC ................................................ 356/432–444
See application file for complete search history.

(56) References Cited

U.S. PATENT DOCUMENTS

2012/0188549 A1* 7/2012 Hoshino et al. ............... 356/437

* cited by examiner

*Primary Examiner* — Tri T Ton

(57) ABSTRACT

A method and apparatus for detecting trace gas concentrations in the atmosphere. An absorption signal is provided that includes collected sunlight that has undergone absorption by a trace gas. The absorption signal is mixed with laser light at a nearby frequency to the absorption signal. An amplitude of a resulting RF signal is proportional to the concentration of the trace gas.

20 Claims, 5 Drawing Sheets

MINIATURIZED LASER HETERODYNE RADIOMETER FOR CARBON DIOXIDE, METHANE AND CARBON MONOXIDE MEASUREMENTS IN THE ATMOSPHERIC COLUMN

The invention described herein was made by an employee of the United States Government, and may be manufactured and used by or for the Government for governmental purposes without the payment of any royalties thereon or therefor.

FIELD

The aspects of the present disclosure relate generally to the field of laser heterodyne radiometry and in particular to a system and method for detecting trace gas concentrations in the atmosphere.

BACKGROUND

Laser heterodyne radiometry is a technique for detecting weak absorption signals that was adapted from radio receiver technology. In a radio receiver, a weak input signal from a radio antenna is mixed with a stronger local oscillator signal. The mixed signal (beat note, or intermediate frequency (IF)) has a frequency equal to the difference between the input signal and the local oscillator. The intermediate frequency is amplified and sent to a detector that extracts the audio from the signal.

Since approximately 1971, laser heterodyne radiometers (LHR) have been used for atmospheric studies. The laser heterodyne receiver was originally developed for Earth studies and has demonstrated measurement of atmospheric ozone concentration profiles from the ground. A LHR is generally able to make measurements with an ultrahigh spectral resolution over a narrow range. In a laser heterodyne radiometer, the weak input signal is light that has undergone absorption by a trace gas. The local oscillator (LO) is a laser at a near-by frequency to the weak input signal. The two light waves are superimposed in a beam splitter or single mode fiber coupler, mixed in the high speed detector and the RF beat signal is extracted. Changes in the concentration of the trace gas are realized through analyzing changes in the beat frequency amplitude. The heterodyne method generally down-converts the received signal to a lower, intermediate frequency (IF) signal in order to process it more easily Satellite instruments that measure carbon cycle gases in the atmospheric column need comparable ground validation measurements. The only network that currently measures carbon dioxide ($CO_2$) and methane ($CH_4$) in the atmospheric column is the Total Carbon Column Observing Network (TCCON). The TCCON is a network of ground-based Fourier Transform Spectrometers that record direct solar spectra in the near-infrared spectral region. For these spectra, accurate and precise column-averaged abundance of $CO_2$, $CH_4$, $N_2O$, HF, $H_2O$ and HDO are retrieved. Only two of the TCCON operational sites are in the United States. TCCON data is used for validation of GOSAT data, and will be used for OCO 2 validation.

The existing network of ground Fourier Transform Spectrometer instruments making column measurements is sparse because cost and size limit their viability as a mass-produced ground network instrument. While the Fourier Transform Spectrometers of the TCCON network can measure the largest range of trace gases, the TCCON network is severely limited due to the high cost and extreme size of these instruments. Typically, these instruments occupy small buildings and require personnel for operation. It would be advantageous to provide a significantly small autonomous instrument that can be incorporated into the Aerosol Robotic Network (AERONET) program's much larger global network. AERONET is a globally distributed network of more than 450 land based aerosol sensing instruments (autonomous sun photometers).

Accordingly, it would be desirable to provide a laser heterodyne radiometer system that addresses at least some of the problems identified above.

BRIEF DESCRIPTION OF THE DISCLOSED EMBODIMENTS

As described herein, the exemplary embodiments overcome one or more of the above or other disadvantages known in the art.

One aspect of the exemplary embodiments relates to a method for detecting trace gas concentration in the atmosphere. In one embodiment, the method includes providing an absorption signal comprising collected sunlight that has undergone absorption by a trace gas, and mixing the absorption signal with laser light at a nearby frequency to the absorption signal, where an amplitude of a resulting RF signal is proportional to the concentration of the trace gas.

Another aspect of the exemplary embodiments related to a laser heterodyne radiometer for detecting trace gas measurements in an atmospheric column. In one embodiment, the radiometer includes a modulator configured to modulate incoming sunlight that contains an absorption signal of a trace gas, a local oscillator configured to generate a light signal at a nearby wavelength to the absorption signal, a single mode fiber coupler configured to superimpose the absorption signal and the light signal, a detector configured to mix the superimposed signals and produce a RF beat frequency, wherein an amplitude of the RF beat frequency is proportional to a concentration of the trace gas in the atmosphere.

A further aspect of the exemplary embodiments is directed to a system for detecting trace gas concentrations in an atmosphere. In one embodiment, the system includes an optics system configured to collect sunlight and detect an absorption signal of a trace gas in the collected sunlight and a laser heterodyne radiometer. The laser heterodyne radiometer includes a local oscillator in the form of a laser that produces a light signal and a detector that mixes the absorption signal and the laser light signal to produce an RF beat signal. The concentration of trace gas is detected as a function of changes in an amplitude of the RF beat signal.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

The accompanying drawings illustrate presently preferred embodiments of the present disclosure, and together with the general description given above and the detailed description given below, serve to explain the principles of the present disclosure. As shown throughout the drawings, like reference numerals designate like or corresponding parts.

DETAILED DESCRIPTION OF THE EXEMPLARY EMBODIMENTS OF THE DISCLOSURE

Figure 1:
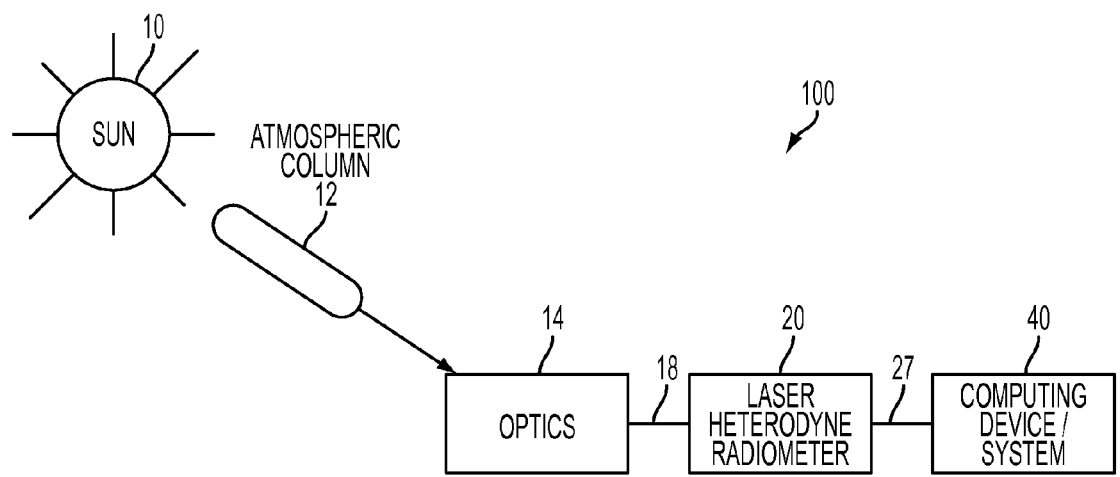
FIG. 1 illustrates a block diagram of one embodiment of a system incorporating aspects of the present disclosure.

Referring to FIG. 1, an exemplary system for measuring greenhouse gases in the atmosphere and resolving their concentrations at different altitudes is generally designated by reference numeral 100. The aspects of the disclosed embodiments provide a laser heterodyne radiometer (LHR) that measures greenhouse gases in the atmosphere and resolves their concentrations at different altitudes. Sunlight that has undergone absorption by a greenhouse gas is collected, and the weak absorption signal is amplified by mixing it with telecommunications laser light at a near-by frequency. The resulting RF signal is proportional to the concentration of the greenhouse gas. Although the embodiments disclosed herein will be described with reference to the drawings, it should be understood that the embodiments disclosed herein can be embodied in many alternate forms. In additional any suitable size, shape or type of elements or materials could be used.

Referring to FIG. 1, the laser heterodyne radiometer 20 is configured to receive a weak input signal 18 from an optical system 14, which in one embodiment includes a collimation optical system. The optical system 14 is generally configured to collect sunlight 10 that includes an absorption signal of a trace gas. The optical system 14 can include, or be coupled to a sun tracking system that is used to point the collection optics 14 at the sun and track the sun throughout the day.

In the embodiments described herein, the weak input signal 18 is sunlight that has undergone absorption by a trace gas, also referred to as a greenhouse gas. For purposes of the description herein, the trace gases of interest include $CO_2$, $CH_4$ and CO. The measurements of $CO_2$, $CH_4$ and CO are in the range of approximately 1.5 to 1.6 microns. Specifically, $CO_2$ is measured at 1.573 microns, $CH_4$ at 1.612 microns and CO at 1.564 microns. These wavelengths are much shorter than wavelengths previously used in laser heterodyne radiometers.

The weak input signal 18 is processed in a laser heterodyne radiometer 20 to generate an RF beat signal 27. The RF heat signal 27 is sensitive to changes in absorption and is located at an easier-to-process RF frequency in the range of approximately 10 to 500 MHz. The changes in concentration of the trace gas(es) are realized through analyzing changes in the amplitude of the beat signal 27 as the laser heterodyne radiometer 20 scans through the wavelength of the absorption feature. In one embodiment, a computer 40, or other suitable computing device or system is configured to receive the RF beat signal 27, determine the trace gas concentrations and provide that information in a suitable format.

Figure 2:
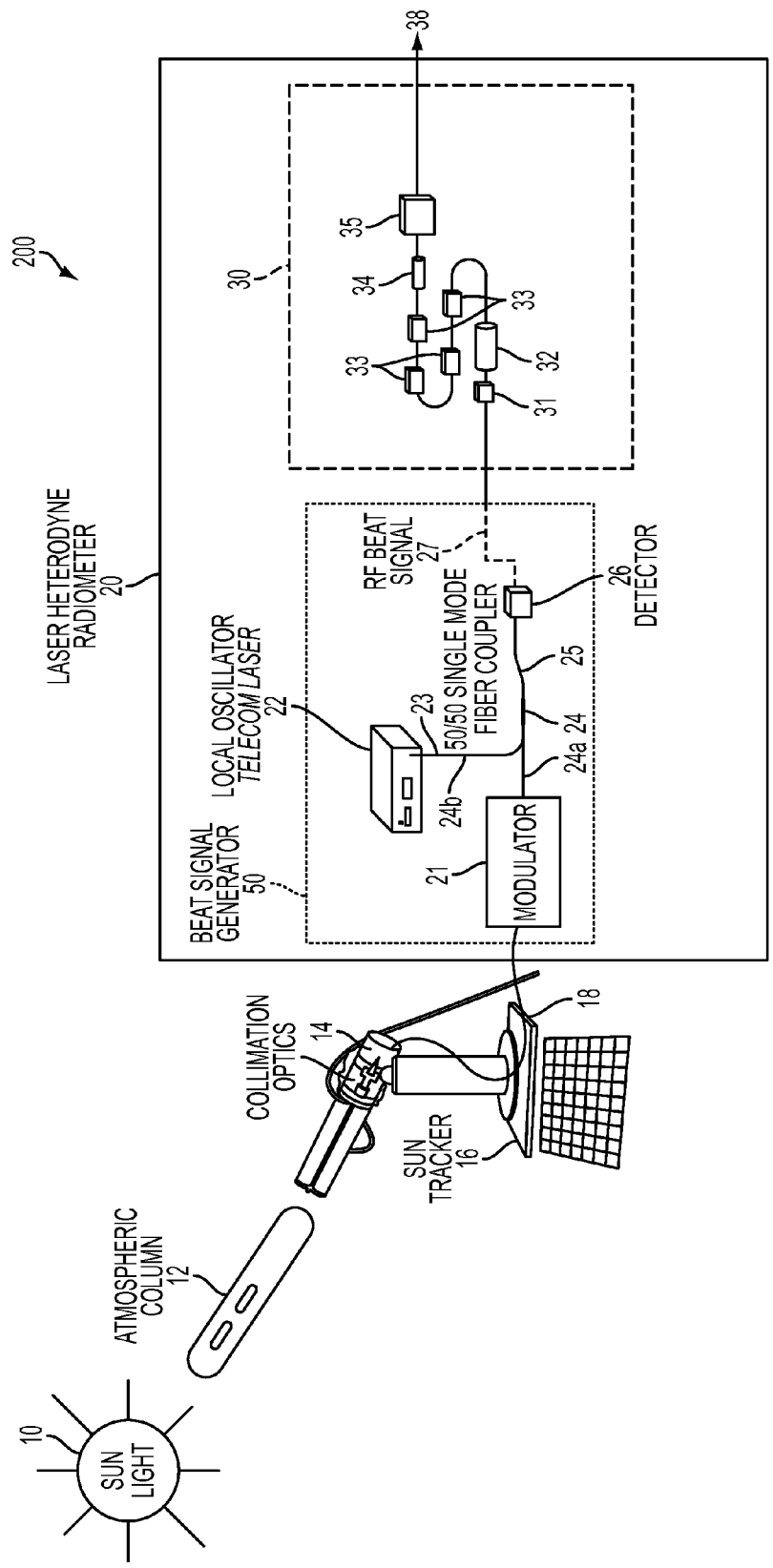
FIG. 2 illustrates a block diagram of an embodiment of a system incorporating aspects of the present disclosure.

Referring to FIG. 2, another embodiment of a system 200 incorporating aspects of the present disclosure is illustrated. In the embodiment shown in FIG. 2, the laser heterodyne radiometer 20 includes a beat signal generator 50 and an RF receiver and signal processing system 30. In one embodiment, the beat signal generator 50 is configured to produce the RF beat signal 27 described above. The RF receiver system 30 is configured to process the RF beat signal 27 and increase the power level of the beat signal 27 to a measurable level while minimizing any noise.

In the example of FIG. 2, the beat signal generator 50 includes a local oscillator 22. In the embodiments described herein, the local oscillator 22 comprises a telecommunication laser. In one embodiment, the local oscillator 22 comprises a distributed feedback laser. The input signal 18, also referred to herein as the absorption signal 18, is mixed with the laser light 23 produced by the local oscillator 22 at a near-by frequency to the weak input, signal 18. In alternate embodiments, the local oscillator 22 can include diode lasers, quantum cascade lasers and optical fiber lasers.

In one embodiment, the laser light 23 produced by the local oscillator 22 and the absorption signal 18 are superimposed in either a beam splitter or a single mode fiber coupler 24 and then mixed in a detector 26, such as a fast photoreceiver. The detector 26 receives the superimposed light signal 25 and is configured to produce the RF beat signal 27. The RF beat signal 27 is sensitive to changes in absorption and is located at an easier-to-process RF frequency in the range of approximately 10 to 500 MHz. The changes in concentration of the trace gas(es) are realized through analyzing changes in the amplitude of the beat signal 27 as the laser 22 scans through the wavelength of the absorption feature.

Referring still to FIG. 2, in one embodiment, the sunlight 10 that has undergone absorption by a trace gas in the atmospheric column 12 is collected with collimation optics 14, which in this example includes or is coupled to a sun tracker system 16. For purposes of the description herein, the sun tracker system 16 is referred to as an AERONET sun tracker system. The collection of the sunlight can include collecting the sunlight with a collimator and launching the signal into a single mode optical fiber. The sunlight exits the single mode optical fiber and is collimated.

In one embodiment, the absorption signal 18 is modulated with an optical chopper 21 and introduced into the laser heterodyne radiometer 20 through a single mode optical fiber. In one embodiment, the modulated light is launched into a branch 24a of a single mode fiber coupler 24. In this embodiment, the light 23 from the local oscillator 22, which in this example is a telecommunications laser, is launched into a branch 24b of the single mode optical coupler 24, and is superimposed on the absorption signal 18 in the single mode fiber coupler 24. The superimposed light signal 25 from the fiber coupler 24 is mixed in the detector 26, to produce the RF beat signal 27. In one embodiment, the detector 26 comprises an ultra-fast (5 GHz) Indium Gallium Arsenide (InGaAs) photodiode detector. The output of the detector 26 is the RF beat signal 27.

In one embodiment, referring to FIG. 2, the RF beat signal 27 is processed in an RF receiver 30. The RF receiver 30 is generally a high gain, low noise amplifier that increases the power level of the beat signal 27 to a measurable level while adding as little noise to the measurement as possible. In the embodiment shown in FIG. 2, the RF receiver 30 includes a bias-T device 31, filter 32, amplifiers 33, detector 34 and a video amplifier 35. In alternate embodiments, any suitable RF receiver device can be used that will increase the power level of the beat signal 27 will minimal noise. In one embodiment, the beat signal 27 from the detector 26 passes through a bias-T device 31, with a 50-ohm resistor and a low pass filter, to separate the RF and DC outputs of the detector 26. The signal passes through the filter 32, which in one embodiment comprises a low pass filter, which determines the resolution bandwidth. The amplifiers 33 increase the signal gain. The detector 34 outputs a voltage proportional to the input power. In this embodiment, a video amplifier 35 is used to amplify and low-pass filter the output from the RF detector 34. The output 38 of the video amplifier 35, the amplitude of the beat signal 27, is monitored as the laser 22 scans across the wavelength region of a rotational-vibrational gas absorption feature.

In one embodiment, the filter 32 shown in FIG. 2, comprises a band-pass filter. In one embodiment, the filter 32 is configured to select the dual-sideband frequencies around the laser that are measured. Due to the dual-sideband properties of the measurement, the frequency resolution of the final measurement will be twice the upper cutoff frequency of the band-pass filter 32. The lower cutoff frequency of the band-pass filter 32 exists only to reduce an amount of approximately 1/f noise in the system 200.

In the example of FIG. 2, after filtering 32 and amplification 33, RF detection is performed with a detector 34. In one embodiment, the detector 34, which can comprise a square law detector, is configured to output a voltage that is equal to the square of the input voltage, allowing the measurement of the RF signal. The output of the square law detector 34 is generally a very low voltage with significant bandwidth. Thus, in one embodiment, the output of the detector 34 can also be processed with an operational amplifier, such as a video amplifier and low pass filter circuit, generally shown as 35, to provide a less noisy average measurement. The final output voltage from the detector 34 is proportional to the RF power coming into the radiometer 20 combined with system noise. Scanning the laser 22 through an absorption feature in the infrared results in the scanned beat signal 27 in the RF. Deconvolution of the beat signal 27 through the retrieved algorithm allows for the extraction of altitude contributions to the column signal.

Figure 3:
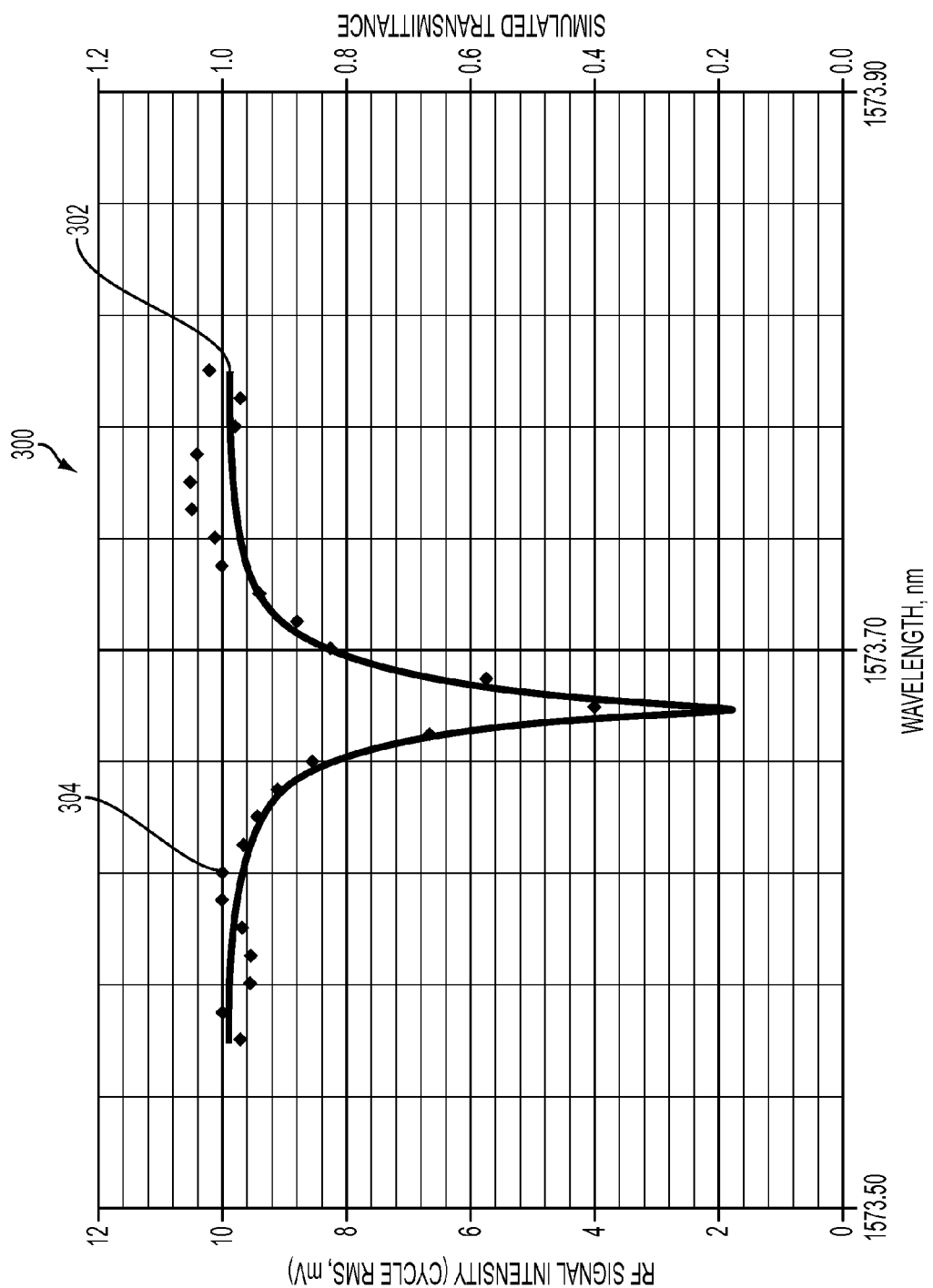
FIG. 3 illustrates a graphical representation of the amplitude of the beat signal as the laser scans across the wavelength of a rotational-vibrational gas absorption feature of carbon dioxide (C02).

FIG. 3 presents a graphical illustration 300 of one embodiment of the output from the video amplifier 35 for a measurement of $CO_2$ transmittance in the atmospheric column (absorption=1−transmittance). The data points, generally indicated by the reference 304, were taken by scanning the laser from 1,57356 microns to 1.57380 microns in 0.00001 micron increments while recording the amplitude of the signal 38, the output of the video amplifier 35, as a cycle RMS (root mean square) value in mV. The radio frequency intensity, or amplitude of the beat signal in mV is shown as a function of the wavelength of the laser 22. There was no correction in this data for clouds or sun tracker movement. The solid line 302 is a simulated transmittance that uses the US Standard Atmospheric model, and the zenith angle to predict the transmittance of the same $CO_2$ absorption feature at the same time of day. The collected data and simulated data are in excellent agreement. As shown by the graph 300, the depth of the measured line 302 is proportional to the concentration of the gas in the atmospheric column. Because transmittance features are broader at lower altitudes (due to collisional broadening) than at higher altitudes, the wings of this feature will be more heavily weighted to lower altitudes. Consequently, the concentration of $CO_2$ as a function of altitude can also be extracted from this data.

Figure 4:
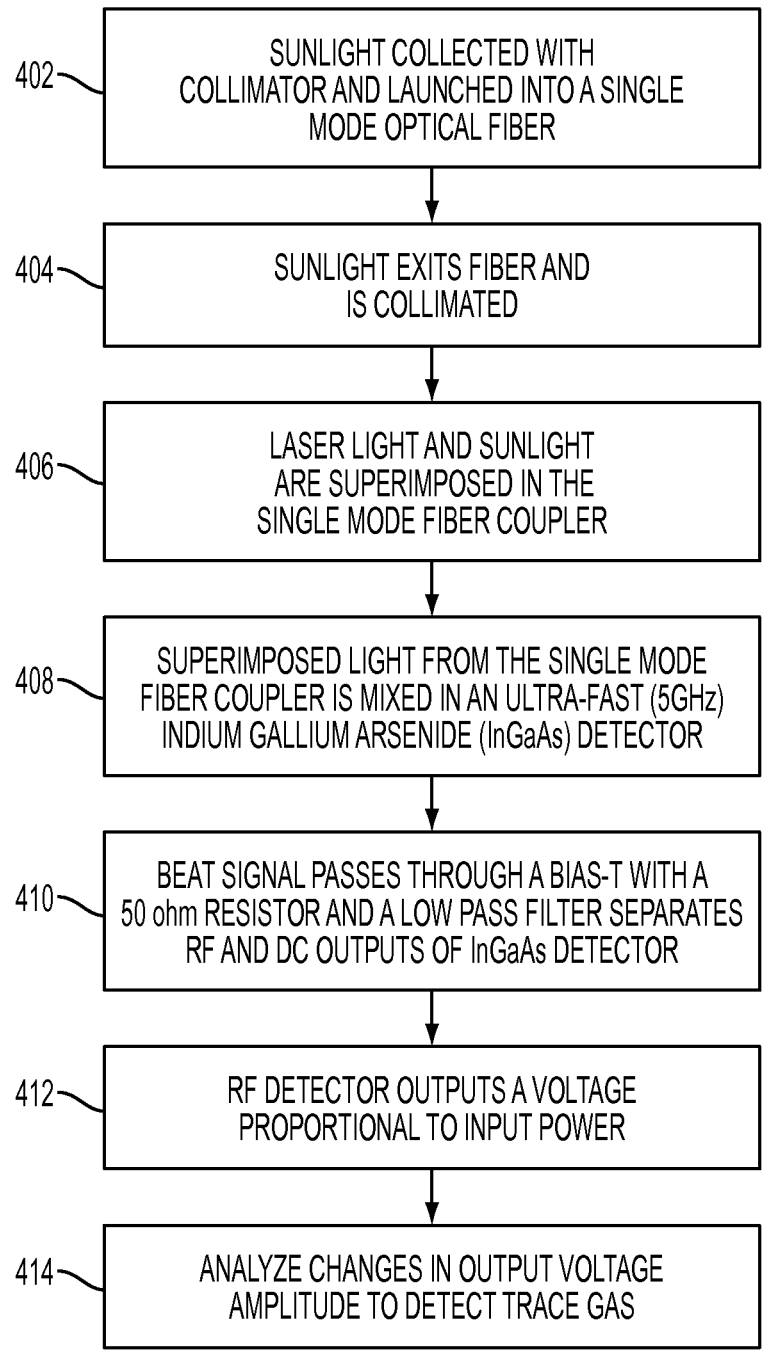
FIG. 4 illustrates a flow chart of one embodiment of a process incorporating aspects of the present disclosure.

Referring to FIG. 4, one embodiment of a process flow incorporating aspects of the present disclosure is illustrated. As shown in FIG. 4, the sunlight is collected 402, and in one embodiment, collimated 404. The collimated light is modulated and superimposed 406 with light from the laser, such as the laser 22 shown in FIG. 2. The superimposed light signals are mixed 408 to generate 410 the RF beat signal. In one embodiment, the RF beat signal is amplified and filtered 412. An output voltage is generated 414, where the output voltage is proportional to the input power. The concentration of trace gas in the atmospheric column and altitude profiles is realized by analyzing 414 changes in the amplitude of the output voltage.

Figure 5:
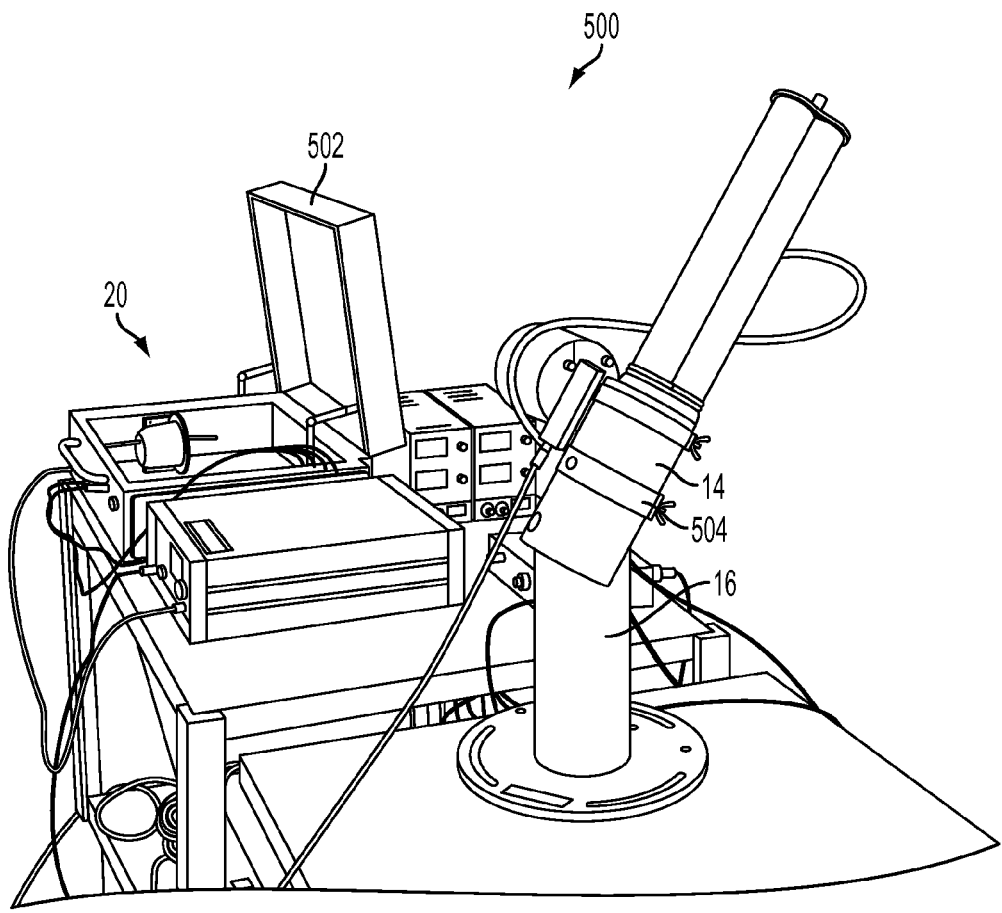
FIG. 5 illustrates a perspective view of one embodiment of a system application incorporating aspects of the present disclosure.

Referring to FIG. 5, one embodiment of a system application 500 of the laser heterodyne radiometer system 100 incorporating aspects of the present disclosure is illustrated. In this exemplary application, the laser heterodyne radiometer 20 of FIG. 1 is mounted in a small suitcase type case 502, to form what can be referred to as a mobile field unit. In this example, the fiber coupled light collection optics 14 are connected to the sun tracker 16 by a clamp 504. The smaller size and portability of the system 500 allows the system 500 of the disclosed embodiments to be considered for use in a global ground network for measuring carbon fluxes in the atmospheric column.

The aspects of the disclosed embodiments measure trace gases in the atmospheric column using sunlight as the light source. The laser heterodyne radiometer of the disclosed embodiments is configured to measure $CO_2$, $CH_4$, and O2 in the atmospheric column, all in a relatively small size and inexpensive, luggage sized package that can be coupled to an AERONET aerosol sensor. The concentration of trace gases in the atmosphere is determined by measuring their absorption of sunlight in the infrared. Each absorption signal is mixed with laser light at a near-by frequency in a fast photoreceiver. The resulting beat signal is sensitive to changes in absorption, and located at an easier to process RF frequency. The entire absorption feature is sampled by scanning the laser across the wavelength region containing this absorption feature. Because different portions of this feature have unique weightings based on the altitudes of the gas sampled, trace gas concentrations can be determined as a function of altitude. As a ground sensor, the laser heterodyne radiometer is configured to operate in tandem with AERONET, coupling to the sun tracker. This allows for simultaneous aerosol measurements for removing cloud and aerosol contributions to trace gas measurements. The laser heterodyne radiometer of the disclosed embodiments can be easily deployed into AERONET's network of instruments worldwide, providing a rapid path to deployment as a global ground instrument and an inexpensive tool for resolving the global carbon budget.

Thus, while there have been shown, described and pointed out, fundamental novel features of the invention as applied to the exemplary embodiments thereof, it will be understood that various omissions and substitutions and changes in the form and details of devices and methods illustrated, and in their operation, may be made by those skilled in the art without departing from the spirit of the invention. Moreover, it is expressly intended that all combinations of those elements and/or method steps, which perform substantially the same function in substantially the same way to achieve the same results, are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for detecting trace gas concentrations in the atmosphere, comprising:
   providing an absorption signal comprising collected sunlight that has undergone absorption by a trace gas contained in the atmosphere; and
   mixing the absorption signal with laser light generated remote from said atmosphere where said sunlight has undergone said absorption by said trace gas, said laser light being at a nearby frequency to the absorption signal, wherein an amplitude of a resulting RF signal is proportional to the concentration of the trace gas.

2. The method of claim 1, comprising resolving the concentration of the trace gas at different altitudes by collecting an entire absorption feature.

3. The method of claim 1, comprising mixing the absorption signal with laser light provided by a distributed feedback telecommunications laser.

4. The method of claim 1, wherein the trace gas comprises one or more of carbon dioxide ($CO_2$), methane ($CH_4$) and carbon monoxide (CO).

5. The method of claim 1, comprising analyzing changes in amplitude of the resulting RF signal to determine changes in the concentration of the trace gas.

6. The method of claim 1, comprising mixing the absorption signal with laser light at the nearby frequency in a fast photoreceiver to generate the resulting RF signal, and analyzing changes in an amplitude of the RF signal to determine changes in the concentration of the trace gas.

7. The method of claim 1, comprising collecting the sunlight with collimation optics that are connected to an AERONET sun tracker system.

8. The method of claim 1, wherein the absorption signal and laser light at a nearby frequency are processed in a laser heterodyne radiometer.

9. A laser heterodyne radiometer for detecting trace gas measurements in an atmospheric column, comprising:
   a modulator configured to modulate incoming sunlight from a remote location that contains an absorption signal of a trace gas existing at said remote location;
   a local oscillator configured to generate a light signal at a nearby wavelength to the absorption signal;
   a single mode fiber coupler configured to superimpose the absorption signal and the light signal; and
   a detector configured to mix the superimposed signals and produce a RF beat frequency, wherein an amplitude of the RF beat frequency is proportional to a concentration of the trace gas in the atmosphere.

10. The laser heterodyne radiometer of claim 9, wherein the local oscillator is a distributed feedback laser.

11. The laser heterodyne radiometer of claim 9, wherein the detector is a fast photoreceiver.

12. The laser heterodyne radiometer of claim 9, wherein the absorption signal comprises sunlight that has undergone absorption by a trace gas.

13. The laser heterodyne radiometer of claim 9, wherein the trace gas comprises one or more of carbon dioxide ($CO_2$), methane ($CH_4$) and carbon monoxide (CO).

14. A system for detecting trace gas concentrations in an atmosphere, comprising:
   an optics system configured to collect sunlight and detect an absorption signal of a trace gas in the collected sunlight; and
   a laser heterodyne radiometer, the laser heterodyne radiometer comprising:
      a local oscillator, the local oscillator comprising a laser to produce a light signal;
      a detector configured to mix the absorption signal and the laser light signal to produce an RF beat signal, wherein the concentration of trace gas is detected as a function of changes in an amplitude of the RF beat signal.

15. The system of claim 14, wherein the aerosol sensor system is an AERONET suntracker system.

16. The system of claim 14, wherein the local oscillator is a telecommunications laser.

17. The system of claim 16, wherein the telecommunications laser is a distributed feedback laser.

18. The system of claim 14, wherein the detector is a fast photoreceiver.

19. The system of claim 14, comprising a receiver/amplification stage configured to increase a power level of the RF beat signal.

20. The system of claim 14, wherein the laser heterodyne radiometer is packaged in a portable case.

* * * * *